United States Patent [19]

Bornengo

[11] 4,172,713

[45] Oct. 30, 1979

[54] ALKALI AND AMMONIUM SALTS OF ZINC BIS-N,N'(DITHIOCARBOXY)-THIAZOLIDIN-4-CARBOXYLIC ACID

[75] Inventor: Mario Bornengo, Massa, Italy

[73] Assignee: Montedison S.p.A., Milan, Italy

[21] Appl. No.: 772,129

[22] Filed: Feb. 25, 1977

[30] Foreign Application Priority Data

Feb. 26, 1976 [IT] Italy .................................. 20615 A/76

[51] Int. Cl.$^2$ .................... A01N 5/00; A01N 9/12; C07F 3/06
[52] U.S. Cl. ........................................ 71/90; 424/245; 548/104; 548/146
[58] Field of Search ............................. 260/299; 71/90; 424/245

[56] References Cited

U.S. PATENT DOCUMENTS

| | | | |
|---|---|---|---|
| 3,943,143 | 3/1976 | Popoff et al. | 260/299 |
| 3,959,304 | 5/1976 | Teach | 260/307 FA |

FOREIGN PATENT DOCUMENTS

| | | |
|---|---|---|
| 1912064 | 7/1970 | Fed. Rep. of Germany. |
| 1539784 | 9/1968 | France. |
| 737277 | 9/1955 | United Kingdom. |

*Primary Examiner*—Donald G. Daus
*Assistant Examiner*—Diana G. Rivers

[57] ABSTRACT

There are disclosed derivatives of thiazolidin-4-carboxylic acid, more particularly alkali and ammonium salts of zinc bis-(N,N'(dithiocarboxy)-(thiazolidin-4-carboxylic acid prevent the infection of plants by fungi and, at the same time, stimulate plant growth. A method for preparing said derivatives is also disclosed.

4 Claims, No Drawings

ALKALI AND AMMONIUM SALTS OF ZINC BIS-N,N'(DITHIOCARBOXY)-THIAZOLIDIN-4-CARBOXYLIC ACID

THE PRIOR ART

The use of thiazolidin-4-carboxylic acid to stimulate the growth of plants is described by Oeriu in Italian Patent No. 804,816, issued to the Rumanian Ministry of Chemical Industry.

It is also known that zinc ethylene-1,2-bis-dithiocarbamate ("Zineb") and other zinc carbamates such as zinc dimethyldithiocarbamate ("Ziram") having low molecular weight aliphatic groups bound to the dithiocarbamic group, are active fungicides.

THE PRESENT INVENTION

This invention provides new alkaline and ammonium salts of zinc bis-N,N'(dithiocarboxy)-thiazolidin-4-carboxylic acid which are both active fungicides and stimulants of plant growth.

The salts of the invention have the following general formula:

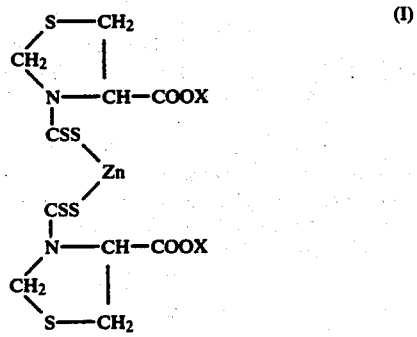

wherein X=K, Na or NH₄.

According to another aspect of this invention, the salts of formula (I) are prepared by treating thiazolidin-4-carboxylic acid, in an alkaline medium, with CS₂, and reacting the alkaline dithiocarbamate of thiazolidin-4-carboxylic acid thus obtained with a zinc salt, e.g., zinc sulphate, adapted to provide the alkaline or ammonium salt of zinc bis-N,N'(dithiocarboxy)-4-carboxylic acid, according to the following reaction:

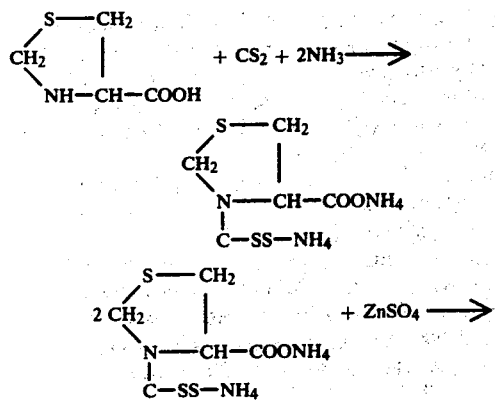

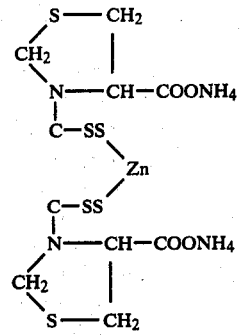

The reagents may be added to the reactor at temperature of from room temperature to 100° C. Preferably, when the reaction is carried out in aqueous alkali, the carbon disulphide is added at a temperature of 38° C. to 40° C. It is not necessary to isolate the alkaline dithiocarbamate of thiazolidin-4-carboxylic acid from the crude, or total, reaction product, since zinc dithiocarbamate of thiazolidin-4-carboxylic acid is insoluble in water and in most organic solvents.

The finished product can be dried in an oven in vacuo, preferably at a temperature of 80° C.-90° C.

The alkaline and ammonium salts of zinc bis-N,N'(dithiocarboxy)-thiazolidin-4-carboxylic acid of the invention are unique in that, being as effective in combatting infection of plants by fungi as the most effective of the known fungicidally active dithiocarbamates, these salts stimulate the growth of plants at least as effectively as the known salts of thiazolidin-4-carboxylic acid. This is surprising and an unobvious result, taking account of the facts that the latter property is not exhibited by mixtures of zinc ethylene-1,2-bis-dithiocarbamate and salts of thiazolidin-4-carboxylic acid (see Example 3 infra), and that the best zinc dithiocarbamates are the simplest, i.e., those having the dithiocarbamatic group or groups bound to an aliphatic molecule having only a low carbon atom content.

Furthermore, by using the compounds of this invention it is possible to alternate, in the long run, fungifighting treatments with usual fungi-fighting compounds and with the growth-stimulating and fungifighting compounds of the present invention or to obtain the same result by a single treatment with the compounds of the invention or to suitably mix the agents to achieve simultaneous growth stimulation and fungicombatting action.

The tests relating to the fungi-fighting activity of the compounds of the invention in comparison with that of "Zineb", and the tests concerning the stimulating activity in vines already treated with "Zineb" (alternating the treatments with zinc ethylene 1,2-bis-dithiocarbamate with a mixed treatment) are reported in Examples 2 and 3, infra.

The following examples are given to illustrate the invention in more detail and are not intended to be limiting.

EXAMPLE 1

Preparation of the ammonium salt of zinc bis-N,N'(dithiocarboxy)-thiazolidin-4-carboxylic acid.

A flask equipped with thermometer, stirrer, dropping funnel and reflux cooler was charged, in order given, with:

water: 550 g

28% solution of NH₄OH: 290 g (4.8 moles)

Thiazolidin-4-carboxylic acid (99%): 270 g (2.0 moles).

The solution was brought to 38°-40° C. and 160 g (2.1 moles) of CS₂ were added dropwise over a period of 1 hour. At the conclusion of dropping, the mass was reacted for a further 1 hour, at the same temperature.

The homogeneous, light yellow solution consisted of an aqueous solution of thiazolidin-4-carboxylic acid ammonium dithiocarbamate, to which a 10% solution of ZnSO₄ (1,750 g; 1.1 moles) was added under stirring.

A mustard-colored precipitate was obtained; the slurry was kept under stirring for 1 hour at 30° C., whereupon it was filtered, washed with water, and dried in an oven under vacuum for 6 hours at 80°-90° C.

The finished product appeared in the form of a hazel-brown powder, that, on analysis, gave the following results:

|   | Theoretical | Found |
|---|---|---|
| C | 23.0% | 22.1% |
| H | 3.5% | 3.59% |
| N | 10.8% | 9.47% |
| S | 37.0% | 36.16% |
| Zn | 12.7% | 12.6% |
| CS titratable (Clarke) | 29.4% | 29.0% |

EXAMPLE 2

Comparison between the protective activity against infections due to *Plasmopora viticola* (Bert C) Bert et de Tomi exerted by the product of this invention, and zinc ethylene-1,2-bis-dithiocarbamate.

Both leaf faces of vines cultivated in pot were uniformly spread with an aqueous suspension of the product of this invention, according to the doses indicated (expressed as equivalent of "Zineb"). Other vines were spread with an aqueous suspension of "Zineb", and still other vines were kept as references. 4, 7, 10 days after the treatment, the infection was effected by using a suspension of *Plasmopora viticola* conidia (200,000 conidia/cm³).

After a 7-day incubation period in a moisture-saturated environment, the entire leaf surface of the reference plants was invaded by the infection (0% of infection-free surface), while the percentage of infection-free surface of the treated plants was as reported in Table I. The percentage of leaf surface free from infection, the doses of spread aqueous suspension of active matter and the days in which the infection was effected are also reported in the Table.

| Dose | Infection After | % of Leaf Surface Free From Infection in the Treated Plants | |
|---|---|---|---|
| % | Days | Product of the Invention | Zineb |
| 2 | 4 | 100 | 100 |
| 1 | 4 | 100 | 100 |
| 0.5 | 4 | 95 | 95 |
| 2 | 7 | 100 | 100 |
| 1 | 7 | 93 | 100 |
| 0.5 | 7 | 94 | 97 |
| 2 | 10 | 70 | 100 |
| 1 | 10 | 60 | 100 |

-continued

| Dose | Infection After | % of Leaf Surface Free From Infection in the Treated Plants | |
|---|---|---|---|
| % | Days | Product of the Invention | Zineb |
| 0.5 | 10 | 55 | 94 |

EXAMPLE 3

5-year vine plants, that had been protected against mildew (*Plasmopora Viticola*) by treatment with 2% "Zineb" applied at the usually prescribed intervals, were spread twice (at a 10-day interval: at the beginning and at the end of the blossoming, respectively) with the following mixture, used instead of two corresponding applications of "Zineb":

Compound of the invention: 0.6 g
"Zineb": 200.0 g
Water: 100.0 l.

Besides being thoroughly protected from mildew, the grape production of the grape vines treated with the ammonium salt of zinc bis-N,N'-(dithiocarboxy)-thiazolidin-4-carboxylic acid was 7.5% greater than the grape production of the vines treated with "Zineb" only.

When a mixture of thiazolidin-4-carboxylic acid and "Zineb" is used, no increase in grape production as compared to that of the vines treated with "Zineb" only can be observed. Conversely, by alternating the "Zineb" treatment with a treatment with thiazolidin-4-carboxylic acid without further additives, an increase of 5-6% in the grape production can be observed.

I claim:

1. Salts of thiazolidine-4-carboxylic acid which exhibit both anti-fungal and plant growth-stimulating activity, and which are ammonium or alkali salts of zinc-bis-N,N'-(dithiocarboxy)-thiazolidin-4-carboxylic acid having the formula

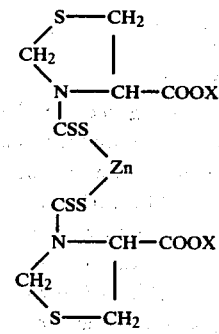

in which X=NH₄, Na or K.

2. The method of protecting plants from fungi infections and simultaneously stimulating growth of the plants which comprises treating the plants with the ammonium or alkali salts of zinc bis-N,N'-(dithiocarboxy)-thiazolidin-4-carboxylic acid according to claim 1, in a dosage of at least 0.5%.

3. The method of claim 2, in which the plants are treated with the ammonium salt of zinc bis-(dithiocarboxy)-thiazolidin-4-carboxylic acid.

4. The method of claim 2, in which the plants are treated with a mixture of the alkali, including ammonium, salt of zinc bis-(dithiocarboxy)-thiazolidin-4-carboxylic acid with another agent which exhibits anti-fungi activity and/or plant-growth stimulating activity.

* * * * *